United States Patent [19]

Mohrs et al.

[11] Patent Number: 5,179,106
[45] Date of Patent: Jan. 12, 1993

[54] SUBSTITUTED N-(QUINOLIN-2-YL-METHOXY) BENZYL-SULPHONYLUREA LEUKOTRIENE SYNTHESIS INHIBITORS

[75] Inventors: Klaus Mohrs, Wuppertal; Siegfried Raddatz; Romanis Fruchtmann, both of Cologne; Christian Kohlsdorfer, Erftstadt; Reiner Müller-Peddinghaus; Pia Theisen-Popp, both of Bergisch-Gladbach, all of Fed. Rep. of Germany

[73] Assignee: Bayer Aktiengesellschaft, Leverkusen, Fed. Rep. of Germany

[21] Appl. No.: 558,730

[22] Filed: Jul. 27, 1990

[30] Foreign Application Priority Data

Aug. 19, 1989 [DE] Fed. Rep. of Germany ....... 3927369

[51] Int. Cl.$^5$ .................. A01N 43/42; C07D 215/36; C07D 215/38
[52] U.S. Cl. ..................... 514/311; 546/175
[58] Field of Search .............. 546/175; 514/311

[56] References Cited

U.S. PATENT DOCUMENTS

| | | | |
|---|---|---|---|
| 4,826,987 | 5/1989 | Nielsen et al. | 546/174 |
| 4,876,346 | 10/1989 | Musser et al. | 546/175 |
| 4,920,132 | 4/1990 | Huang et al. | 546/175 |

FOREIGN PATENT DOCUMENTS

| | | |
|---|---|---|
| 0029982 | 6/1981 | European Pat. Off. |
| 0232954 | 8/1987 | European Pat. Off. |
| 0261539 | 3/1988 | European Pat. Off. |
| 8806886 | 9/1988 | European Pat. Off. |

OTHER PUBLICATIONS

W. Forth, Allgemeine und Spezielle Pharmakologie und Toxikologie, 4th Edition, 1983.
JP 82 64 675, Application 80/140 091, Agricultural Chemistry, p. 6, Week E21, J5–C.

*Primary Examiner*—C. Warren Ivy
*Assistant Examiner*—Raymond Covington
*Attorney, Agent, or Firm*—Sprung Horn Kramer & Woods

[57] ABSTRACT

Inhibiting leucotriene synthesis in patients with novel substituted N-(quinolin-2-yl-methoxy)benzylsulphonylurea of the formula

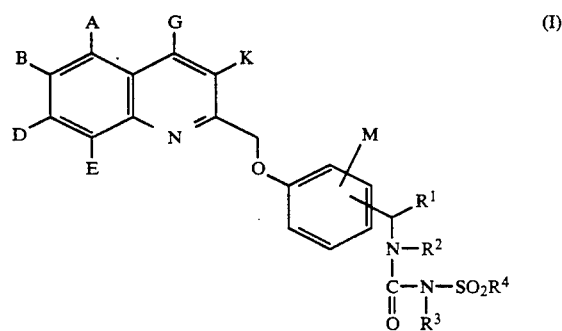

in which
A, B, D, E, G, K and M each independently is H, OH, halogen, $CF_3$, $OCF_3$, COOH, alkyl, alkoxy, alkoxycarbonyl or aryl,
$R^1$ is alkyl or cycloalkyl,
$R^2$ and $R^3$ each independently is H or alkyl, and
$R^4$ is alkyl, aryl or a heterocyclic radical,
and salts thereof.

9 Claims, No Drawings

SUBSTITUTED N-(QUINOLIN-2-YL-METHOXY) BENZYL-SULPHONYLUREA LEUKOTRIENE SYNTHESIS INHIBITORS

The invention relates to substituted N-(quinolin-2-yl-methoxy)benzyl-sulphonylureas, processes for their preparation and their use in medicaments.

It is known that sulphonylureas have an antidiabetic action (compare W. Forth, Allgemeine und Spezielle Pharmakologie und Toxikologie (General and specific pharmacology and toxicology), 4th edition, 1983, B.I.-Wissenschaftsverlag). N,N-dimethyl-N'-[3-(2-quinolyl-methoxy)phenylureas have furthermore been described in JP 82 64 675, Application 80/140 091.

Pyridyl- and quinolylamines which exhibit a specific 5-lipoxygenase inhibition are moreover described in U.S. Pat. No. 4,826,987.

N-(quinolin-2-yl-methoxy)benzyl-sulphonylureas of the general formula (I),

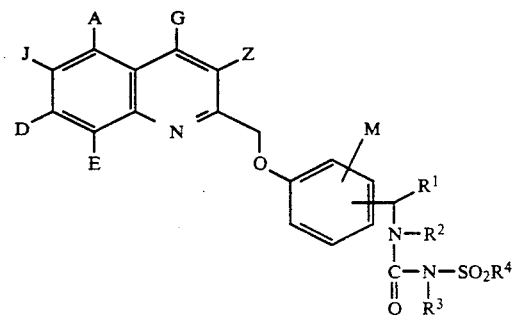

in which

A, J, D, E, G, Z and M are identical or different and represent hydrogen, hydroxyl, halogen, trifluoromethyl, trifluoromethoxy or carboxyl,
represent straight-chain or branched alkyl having up to 10 carbon atoms, which is optionally substituted by hydroxyl or halogen,
represent straight-chain or branched alkoxy or alkoxycarbonyl having up to 10 carbon atoms, or
represent aryl having 6 to 10 carbon atoms, which is optionally substituted by halogen, nitro, cyano or by straight-chain or branched alkyl or alkoxy having up to 8 carbon atoms, $R^1$ represents straight-chain or branched alkyl having up to 10 carbon atoms, which is optionally substituted by alkoxy having up to 8 carbon atoms, halogen or cycloalkyl having 3 to 8 carbon atoms, or
represents cycloalkyl having 3 to 8 carbon atoms, which is optionally substituted by halogen or straight-chain or branched alkyl having up to 8 carbon atoms, $R^2$ and $R^3$ are identical or different and
represent hydrogen or straight-chain or branched alkyl having up to 10 carbon atoms, which is optionally substituted by halogen, hydroxyl or by aryl having 6 to 10 carbon atoms, and $R^4$ represents straight-chain or branched alkyl having up to 10 carbon atoms, which is optionally substituted by halogen, nitro, cyano, hydroxyl, trifluoromethyl or by aryl having 6 to 10 carbon atoms,
or represents a 5- to 7-membered heterocyclic radical having up to 4 different heteroatoms from the series comprising sulphur, oxygen and nitrogen, or represents aryl having 6 to 10 carbon atoms, the heterocyclic radical and the aryl radical optionally being substituted by up to 3 identical or different substituents from the group comprising halogen, nitro, cyano, hydroxyl, straight-chain or branched alkyl, alkylthio and alkoxy having up to 8 carbon atoms, trifluoromethyl and trifluoromethoxy, and salts thereof, have now been found.

Physiologically acceptable salts are preferred in the context of the present invention. Physiologically acceptable salts of the substituted N-(quinolin-2-yl-methoxy)benzyl-sulphonylureas can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts in the context of the present invention are moreover salts of monovalent metals, such as alkali metals, and the ammonium salts. Sodium, potassium and ammonium salts are preferred.

Preferred compounds of the general formula (I) are those in which

A, J, D, E, G, Z and M are identical or different and represent hydrogen, fluorine, chlorine, trifluoromethoxy or carboxyl,
represent straight-chain or branched alkyl having up to 8 carbon atoms, which is optionally substituted by hydroxyl, fluorine, chlorine or bromine,
represent straight-chain or branched alkoxy or alkoxycarbonyl having up to 8 carbon atoms, or
represent phenyl, which is optionally substituted by fluorine, chlorine, bromine, nitro, cyano or by straight-chain or branched alkyl or alkoxy having up to 6 carbon atoms, $R^1$ represents straight-chain or branched alkyl having up to 8 carbon atoms, which is optionally substituted by hydroxyl, fluorine, chlorine, alkoxy having up to 6 carbon atoms or by cyclopropyl, cyclobutyl, cyclopentyl, cyclohexyl or cycloheptyl,
represents cyclopropyl, cyclobutyl, cyclopentyl, cyclohexyl or cycloheptyl, which is optionally substituted by fluorine, chlorine, or straight-chain or branched alkyl having up to 6 carbon atoms, $R^2$ and $R^3$ are identical or different and
represent hydrogen or straight-chain or branched alkyl having up to 8 carbon atoms, which is optionally substituted by fluorine or chlorine, and $R^4$ represents straight-chain or branched alkyl having up to 8 carbon atoms, which is optionally substituted by fluorine, chlorine, nitro, cyano, hydroxyl or by phenyl,
or represents phenyl, which is optionally substituted by up to 2 identical or different substituents from the group comprising fluorine, chlorine, bromine, nitro, cyano, hydroxyl, straight-chain or branched alkyl, alkylthio and alkoxy having up to 6 carbon atoms, trifluoromethyl and trifluoromethoxy, and salts thereof.

Particularly preferred compounds of the general formula (I) are those in which

A, J, D, E, G, Z and M are identical or different and represent hydrogen, fluorine, chlorine, or straight-chain or branched alkyl or alkoxy having up to 6 carbon atoms, $R^1$ represents straight-chain or branched alkyl having up to 6 carbon atoms, which is optionally substituted by fluorine, chlorine or alkoxy having up to 4 carbon atoms or by cyclopropyl, cyclopentyl or cyclohexyl, or represents cyclobutyl, cyclopentyl, cyclohexyl or cycloheptyl, which is optionally substituted by straight-chain or branched alkyl having up to 4 carbon atoms or by fluorine, $R^2$ and $R^3$ are identical or different and represent hydrogen or straight-chain or branched alkyl having up to 6 carbon atoms, and $R^4$ represents straight-chain or branched alkyl having up to 6 carbon atoms, which is optionally substituted by fluorine, chlorine or phenyl, or represents phenyl, which is optionally substituted by fluorine, chlorine, bromine or by straight-chain or branched alkyl having up to 4 carbon atoms, and salts thereof.

Especially preferred compounds of the general formula (I) are those in which the quinolylmethoxy grouping on the phenyl ring is in the 4-position relative to the N-substituted sulphonylurea group.

A process has furthermore been found for the preparation of the compounds of the general formula (I) according to the invention

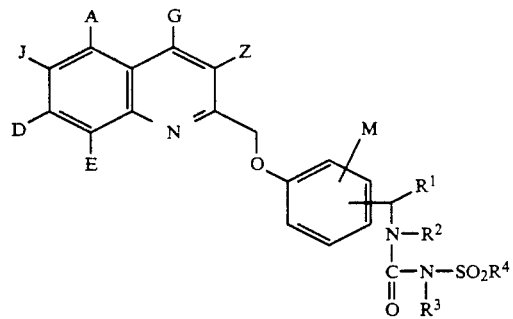

(I)

in which
A, J, D, E, G, Z, M, $R^1$, $R^2$, $R^3$ and $R^4$ have the abovementioned meanings, which is characterized in that amines of the general formula (II)

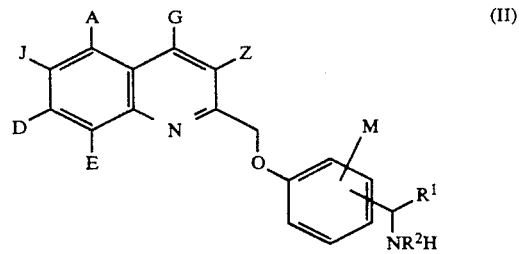

(II)

in which
A, J, D, E, G, Z, M, $R^1$ and $R^2$ have the abovementioned meanings,
are reacted with sulphonyl isocyanates of the general formula (III)

$$R^4-SO_2-NCO \qquad (III)$$

in which
$R^4$ has the abovementioned meaning,
in an inert solvent to give compounds of the general formula (Ia)

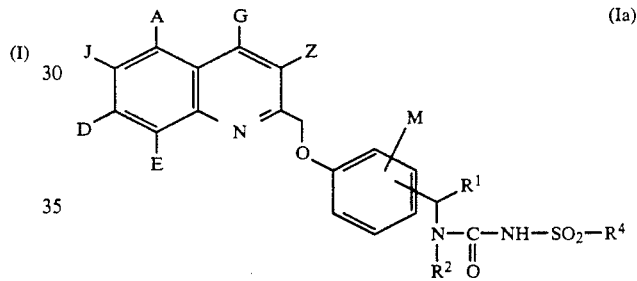

(Ia)

in which
A, J, D, E, G, Z, M, $R^1$, $R^2$ and $R^4$ have the abovementioned meanings,
and in the case of the compounds of the formula (I) where $R^3 \neq H$, the compounds of the formula (Ia) are then alkylated with alkylating agents in inert solvents.

The process according to the invention can be illustrated by the following equation:

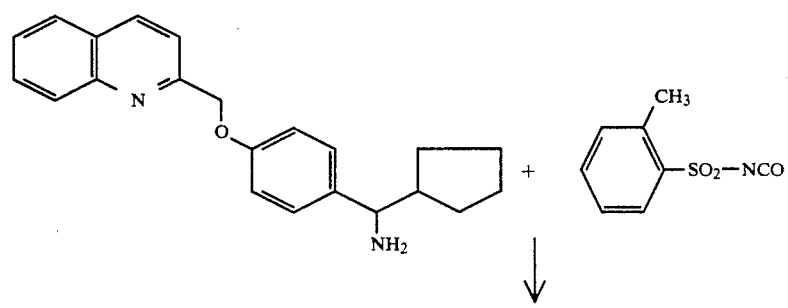

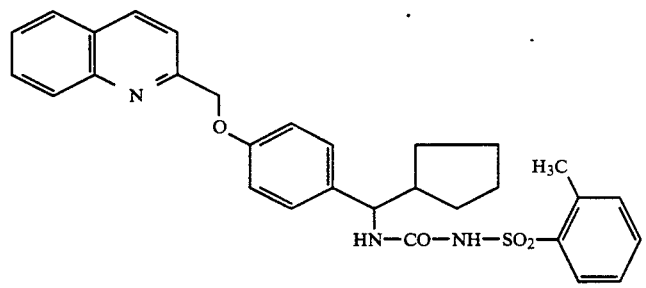

Suitable solvents for the process according to the invention are the customary organic solvents which do not change under the reaction conditions. These include, preferably, ethers, such as diethyl ether, dioxane, tetrahydrofuran or glycol dimethyl ether, or hydrocarbons, such as benzene, toluene, xylene, hexane, cyclohexane or petroleum fractions, or halogenated hydrocarbons, such as methylene chloride, chloroform, carbon tetrachloride, dichloroethylene, trichloroethylene or chlorobenzene, or ethyl acetate, triethylamine, pyridine, dimethyl sulphoxide, dimethylformamide, hexamethylphosphoric acid triamide, acetonitrile, acetone or nitromethane. It is also possible to use mixtures of the solvents mentioned. Methylene chloride is preferred.

The process according to the invention is in general carried out in a temperature range from $-80°$ C. to $+80°$ C., preferably from $-80°$ C. to $0°$ C.

The process according to the invention is in general carried out under normal pressure. However, it is also possible for the process to be carried out under increased pressure or under reduced pressure (for example in a range from 0.5 to 5 bar).

In general, 1 to 3 moles, preferably 1 to 2 moles and particularly preferably 1 mole of sulphonyl isocyanate are employed per mole of the amine.

The sulphonyl isocyanates of the general formula (III) are known or can be prepared by known methods [C. King, J. Org. Chem. 25, 352 (1960); F. Effenberger, R. Gleiter, Chem. Ber. 97, 1576 (1964); H. Ulrich, A.A.R. Sayigh, Angew. Chem. 78, 761 (1966); and Houben-Weyl VIII, 128].

Examples of alkylating agents which can be employed in the process are $(C_1-C_8)$-alkylhalides, sulphonic acid esters or substituted or unsubstituted $(C_1-C_6)$-dialkyl or $(C_6-C_{10})$-diaryl sulphates, preferably methyl iodide, p-toluenesulphonic acid esters or dimethyl sulphate.

The alkylation is carried out in the abovementioned solvents at temperatures of $0°$ C. to $+150°$ C., preferably at room temperatures up to $+100°$ C., under normal pressure.

The amines of the general formula (II) are known in some cases $(R^1=(CH_2)_4CH_3)$, and in this case can be prepared by first reacting compounds of the general formula (IV)

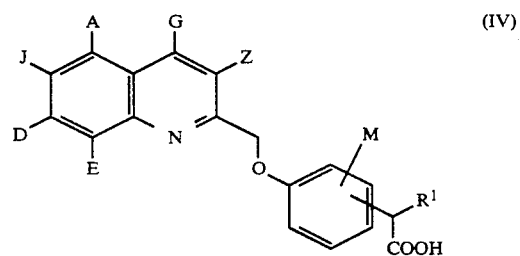

(IV)

in which

A, J, D, E, G, Z, M and $R^1$ have the abovementioned meanings, with azides, such as, for example, phosphoric acid diphenylester-azide or hydrazoic acid, preferably with phosphoric acid diphenylester-azide, in inert solvents, if appropriate in the presence of a base, and then reacting the product with acids by the customary method (conversion of a carboxylic acid into the corresponding amine), nitrogen and carbon dioxide being eliminated, and in the case where $R^2 \neq H$ in the amines of the general formula (II), alkylating the amino group by the abovementioned method.

The process can be illustrated by the following equation:

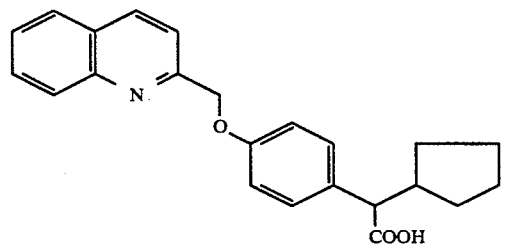

1) + $(C_6H_5)_2P(O)N_3$; $N(C_2H_5)_3$
2) + HCl

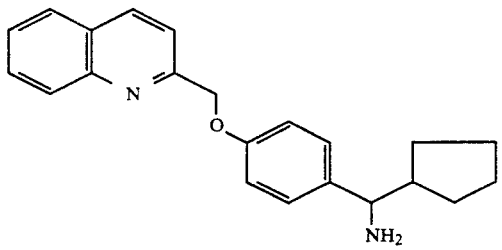

Suitable solvents for degradation of the acid are the abovementioned inert solvents. Dimethylformamide is preferred.

Suitable bases are organic amines (trialkyl)$C_1$-$C_6$)amines) such as, for example, triethylamine, or heterocyclic compounds, such as pyridine, methylpiperidine, piperidine or morpholine. Triethylamine is preferred.

Mineral acids are in general employed as the acids. Hydrochloric acid, hydrobromic acid, sulphuric acid, phosphoric acid or mixtures of the acids mentioned are preferably employed here.

The reaction is carried out in a temperature range from 0° C. to +130° C., preferably from 0° C. to +80° C.

The reaction is in general carried out under normal pressure. However, it is also possible for the process to be carried out under reduced pressure or increased pressure (for example in a range from 0.5 to 5 bar).

Phosphoric acid diphenylester-azide is known (compare J. Am. Chem. Soc. 94, 6203 (1972); J. Org, Chem. 39, 2302 (1974) and Tetrahedron Lett, 1977 (1977)).

The compounds of the general formula (IV) are new and can be prepared, for example, by etherifying compounds of the general formula (V)

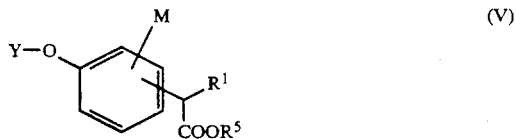

in which
$R^1$ and M have the abovementioned meanings,
$R^5$ represents hydrogen, phenyl or $C_1$-$C_6$-alkyl and
Y represents a typical hydroxyl-protective group, such as, for example, benzyl or tert.-butyl,
with halogenomethylquinolines of the formula (VI)

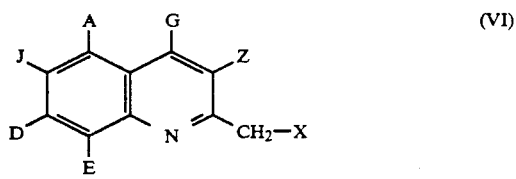

in which
A, J, D, G and Z have the abovementioned meanings, and
X - represents halogen,
by the customary method, after eliminating the protective group Y, and in the case of the acids hydrolyzing the product.

The protective groups are eliminated from the corresponding ethers by the customary method, for example by hydrogenolytic cleavage of the benzyl ethers in the abovementioned inert solvents in the presence of a catalyst using hydrogen gas [compare also Th. Greene: "Protective Groups in Organic Synthesis", J. Wiley & Sons, 1981, New York].

The etherification can be carried out in inert organic solvents, if appropriate in the presence of a base.

Solvents for the etherification can be inert organic solvents which do not change under the reaction conditions. These include, preferably, ethers, such as, for example, dioxane, tetrahydrofuran or diethyl ether, halogenated hydrocarbons, such as methylene chloride, chloroform, carbon tetrachloride, 1,2-dichloroethane or trichloroethylene, hydrocarbons, such as benzene, xylene, toluene, hexane, cyclohexane or petroleum fractions, or nitromethane, dimethylformamide, acetonitrile, acetone or hexamethylphosphoric acid triamide. It is also possible to employ mixtures of the solvents.

Bases which can be employed for the etherification are inorganic or organic bases. These include, preferably, alkali metal hydroxides, such as, for example, sodium hydroxide or potassium hydroxide, alkaline earth metal hydroxides, such as, for example, barium hydroxide, alkali metal carbonates, such as sodium carbonate or potassium carbonate, alkaline earth metal carbonates, such as calcium carbonate, or organic amines (trialkyl(-$C_1$-$C_6$)amines), such as triethylamine, or heterocyclic compounds, such as pyridine, methylpiperidine, piperidine or morpholine.

It is also possible for alkali metals, such as sodium, and hydrides thereof, such as sodium hydride, to be employed as bases.

The etherification is in general carried out in a temperature range from 0° C. to +150° C., preferably from +10° C. to +100° C.

The etherification is in general carried out under normal pressure However, it is also possible for the process to be carried out under reduced pressure or increased pressure (for example in a range from 0.5 to 5 bar).

In general, 0.5 to 5, preferably 1 to 2 moles of halide are employed per mole of the reactant. The base is in general employed in an amount of 0.5 to 5 moles, preferably 1 to 3 moles, based on the halide.

The compounds of the general formula (V) are known per se or can be prepared by the customary method [A. Ulrich, B. Tucker, A.A. R. Sayigh, J. Org. Chem. 31, 2658 (1966)].

The compounds of the general formula (VI) and their preparation are likewise known.

The following halides, for example, can be used according to the invention:
8-chloro-2-chloromethyl-quinoline,
7-chloro-2-chloromethyl-quinoline and
6-fluoro-2-chloromethyl-quinoline.

The carboxylic acid esters are hydrolyzed by customary methods by treating the esters with customary bases in inert solvents, it being possible for the salts initially formed to be converted into the free carboxylic acids by treatment with acid.

Suitable bases for the hydrolysis are the customary inorganic bases. These include, preferably, alkali metal hydroxide or alkaline earth metal hydroxides, such as, for example, sodium hydroxide, potassium hydroxide or barium hydroxide, or alkali metal carbonates, such as sodium carbonate or potassium carbonate, or sodium bicarbonates, or alkali metal alcoholates, such as sodium ethoxide, sodium methoxide, potassium ethoxide, potassium methoxide or potassium tert.-butoxide. Sodium hydroxide or potassium hydroxide is particularly preferably employed.

Suitable solvents for the hydrolysis are water or the organic solvents customary for a hydrolysis. These include, preferably, alcohols, such as methanol, ethanol, propanol, isopropanol or butanol, or ethers, such as tetrahydrofuran or dioxane, or dimethylformamide or dimethyl sulphoxide. Alcohols, such as methanol, ethanol, propanol or isopropanol, are particularly preferably used. It is likewise possible to employ mixtures of the solvents mentioned.

The hydrolysis is in general carried out in a temperature range from 0° C. to +100° C., preferably from +20° C. to +80° C.

The hydrolysis is in general carried out under normal pressure. However, it is also possible for the hydrolysis to be carried out under reduced pressure or under increased pressure (for example from 0.5 to 5 bar).

In carrying out the hydrolysis the base is in general employed in an amount of 1 to 3 moles, preferably 1 to 1.5 moles, per mole of the ester. Molar amounts of the reactants are particularly preferably used.

In carrying out the reaction, in the first steps the salts of the compounds according to the invention are formed as intermediate products, which can be isolated. The acids according to the invention are obtained by treatment of the salts with customary inorganic acids. These include, preferably, mineral acids, such as, for example, hydrochloric acid, hydrobromic acid, sulphuric acid or phosphoric acid. In the preparation of the carboxylic acids, it has proved advantageous here to acidify the basic reaction mixture of the hydrolysis in a second step without isolation of the salts. The acids can then be isolated in the customary manner.

The compounds of the general formula (I) according to the invention surprisingly show a high in vitro activity as leucotriene synthesis inhibitors and a potent in vivo action following oral administration.

The substituted N-(quinolyl-2-yl-methoxy)benzylsulphonylureas according to the invention can be employed as active compounds in medicaments. The substances can act as inhibitors of enzymatic reactions in the context of arachidonic acid metabolism, in particular of 5-lipoxygenase.

They are thus preferably suitable for the treatment and prevention of diseases of the respiratory tract, such as allergies/asthma, bronchitis, emphysema, shock lung, pulmonary hypertension, inflammation/rheumatism and oedemas, thromboses and thromboembolisms, ischaemias (peripheral, cardiac and cerebral disturbances in blood flow), cardiac and brain infarctions, disturbances in cardiac rhythm, angina pectoris and arteriosclerosis, for tissue transplants, dermatoses, such as psoriasis, inflammatory dermatoses, for example eczema, dermatophyte infection, infections of the skin by bacteria and metastases, and for cytoprotection in the gastrointestinal tract.

The substituted N-(quinolyl-2-yl-methoxy)benzylsulphonylureas according to the invention can be used both in human medicine and in veterinary medicine.

The pharmacological action data of the substances according to the invention are determined by the following method:

The release of leucotriene $B_4$ ($LTB_4$) on polymorphonuclear rat leucocytes (PMN) after addition of substances and Ca ionophore was determined by means of reverse phase HPLC according to Borgeat, P. et al., Proc. Nat. Acad. Sci. 76, 2148–2152 (1979) as a measure of the lipoxygenase inhibition. The in vivo activity of the compounds was demonstrated with the mouse ear inflammation model in accordance with the method of Young, J. M. et al., J. of Investigative Dermatology 82, 367–371, (1984).

The new active compounds can be converted in a manner which is known per se into the customary formulations, such as tablets, capsules, coated tablets, pills, granules, aerosols, syrups, emulsions, suspensions and solutions, using inert non-toxic pharmaceutically suitable excipients or solvents. The therapeutically active compound should in each case be present in the formulation here in a concentration of about 0.5 to 90% by weight, preferably 10 to 70% by weight, that is to say in amounts which are sufficient to achieve the stated dosage range.

The formulations are prepared, for example, by extending the active compounds with solvents and/or excipients, if appropriate using emulsifying agents and/or dispersing agents, it being possible, for example in the case where water is used as the diluent, for organic solvents to be used as auxiliary solvents if appropriate.

Examples of auxiliaries which may be mentioned are: water, non-toxic organic solvents, such as paraffins (for example petroleum fractions), vegetable oils (for example groundnut/sesame oil), alcohols (for example ethyl alcohol or glycerol) and glycols (for example propylene glycol or polyethylene glycol), solid excipients, such as natural rock powders (for example kaolins, aluminas, talc or chalk), synthetic rock powders (for example highly-disperse silica or silicates) and sugars (for example sucrose, lactose and glucose), emulsifying agents (for example polyoxyethylene fatty acid esters, polyoxyethylene fatty alcohol ethers, alkylsulphonates and arylsulphonate), dispersing agents (for example ligninsulphite waste liquors, methylcellulose, starch and polyvinylpyrrolidone) and lubricants (for example magnesium stearate, talc, stearic acid and sodium lauryl sulphate).

The administration can be effected in the customary manner, preferably orally or parenterally, in particular perlingually or intravenously. In the case of oral use, tablets can of course also contain, in addition to the excipients mentioned, additives, such as sodium citrate, calcium carbonate and dicalcium phosphate, together with various additional substances, such as starch, preferably potato starch, gelatin and the like. Lubricants, such as magnesium stearate, sodium lauryl sulphate and talc can furthermore be used for tablet-making. In the case of aqueous suspensions and/or elixirs intended for oral uses, various flavor enhancers or dyestuffs can be added to the active compounds, in addition to the abovementioned auxiliaries.

In the case of parenteral use, solutions of the active compounds can be employed, using suitable liquid excipients.

In general it has proved advantageous in the case of intravenous administration to administer amounts of about 0.01 to 10 mg/kg, preferably about 0.01 to 5 mg/kg of body weight to achieve effective results. In the case of oral administration, the dosage is in general about 0.1 to 200 mg/kg, preferably 1 to 100 mg/kg of body weight.

Nevertheless it may at times be necessary to deviate from the amounts mentioned, and in particular to do so as a function of the body weight or the nature of the administration route, or of the individual behavior towards the medicament, the nature of its formulation and the time or interval at which administration takes place. Thus in some cases it may be sufficient to manage with less than the abovementioned minimum amount, whereas in other cases the upper limit mentioned must be exceeded Where relatively large amounts are administered, it may be advisable to distribute these into several individual doses over the course of the day.

Preparation Examples

EXAMPLE 1

1-[4-(quinolin-2-yl-methoxy)phenyl]-1-pentylamine

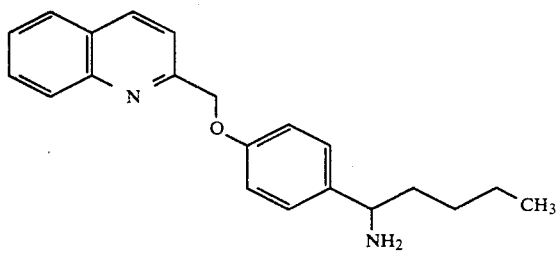

10.5 g (30 mmol) of 2-[4-(quinolin-2-yl-methoxy)phenyl]-caproic acid and 7.7 ml (36 mmol) of phosphoric acid diphenylester-azide are dissolved in 100 ml of dimethylformamide at 0° C. and 10 ml (72 mmol) of triethylamine are added. The mixture is heated at 70° C. for 1 hour and cooled to 0° C., 75 ml of 5 normal hydrochloric acid are added dropwise and the mixture is again heated at 70° C. for 1 hour. The reaction mixture is poured onto water, rendered alkaline with 2-normal sodium hydroxide solution and extracted 5 times with ethyl acetate. After drying over $Na_2SO_4$, the extract is evaporated. The product crystallizes out.

Yield: 8.9 g (92.6% of theory)
Melting point: 97°–100° C.

EXAMPLE 2

[4-(quinolin-2-yl-methoxy)phenyl]-cyclopentyl-methylamine

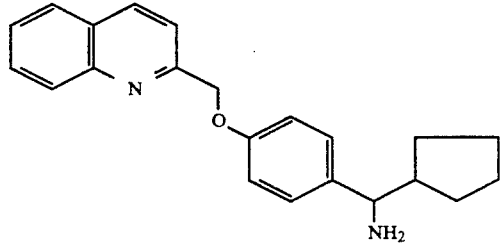

The preparation is carried out analogously to Example 1 from 5 g (13.8 mmol) of 2-[4-(quinolin-2-yl-methoxy)phenyl]-2-cyclopentylacetic acid and 4.57 g (16.6 mmol) of phosphoric acid diphenylester-azide.

Yield: 3.29 g (71.7% of theory)
Melting point: 112° C.

EXAMPLE 3

N-(4-toluenesulphonaminocarbonyl)-1-[4-(quinolin-2-yl-methoxy)phenyl]-1-pentylamine

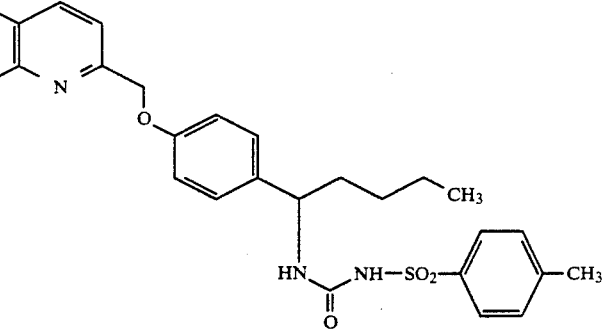

3.2 g (10 mmol) of the compound from Example 1 are dissolved in 50 ml of methylene chloride under inert gas, and 2.2 g (11 mmol) of para-toluenesulphonyl isocyanate are added. The mixture is stirred at 25° C. for 2 hours and concentrated and the residue is chromatographed on silica gel 60 using methylene chloride.

Yield: 4.2 g (80% of theory)
Melting point: 141°–144° C.

EXAMPLE 4

N=(2-toluenesulphonaminocarbonyl)-[4-(quinolin-2-yl-methoxy)phenyl]-cyclopentyl-methylamine

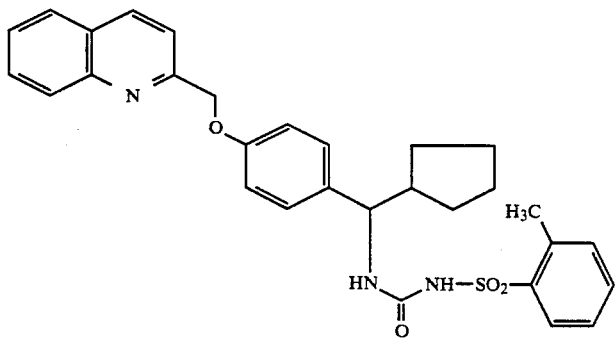

The preparation is carried out analogously to the instructions of Example 3 from 2.84 g (8.5 mmol) of the compound from Example 2 and 1.53 g (7.7 mmol) of 2-toluenesulphonyl isocyanate.

Yield: 3.4 g (83.5% of theory)
Melting point: 207°-211° C.

It is understood that the specification and examples are illustrative but not limitative of the present invention and that other embodiments within the spirit and scope of the invention will suggest themselves to those skilled in the art.

We claim:
1. A substituted N-(quinolin-2-yl-methoxy)benzylsulphonylurea of the formula

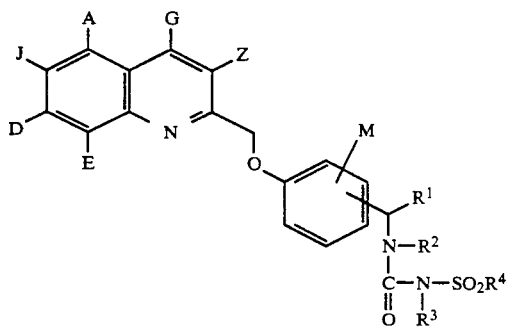

in which
A, J, D, E, G, Z and M are identical or different and represent hydrogen, hydroxyl, halogen, trifluoromethyl, trifluoromethoxy or carboxyl,
represent straight-chain or branched alkyl having up to 10 carbon atoms, which is optionally substituted by hydroxyl or halogen,
represent straight-chain or branched alkoxy or alkoxycarbonyl having up to 10 carbon atoms, or
represent aryl having 6 to 10 carbon atoms, which is optionally substituted by halogen, nitro, cyano or by straight-chain or branched alkyl or alkoxy having up to 8 carbon atoms,
$R^1$ represents straight-chain or branched alkyl having up to 10 carbon atoms, which is optionally substituted by alkoxy having up to 8 carbon atoms, halogen or cycloalkyl having 3 to 8 carbon atoms, or represents cycloalkyl having 3 to 8 carbon atoms, which is optionally substituted by halogen or straight-chain or branched alkyl having up to 8 carbon atoms,
$R^2$ and $R^3$ are identical or different and represent hydrogen or straight-chain or branched alkyl having up to 10 carbon atoms, which is optionally substituted by halogen, hydroxyl or by aryl having 6 to 10 carbon atoms, and
$R^4$ represents straight-chain or branched alkyl, having up to 8 carbon atoms, which is optionally substituted by fluorine, chlorine, nitro, cyano, hydroxyl, or by aryl having 6 to 10 carbon atoms, or phenyl,
or represents phenyl which is optionally substituted by up to 2 identical or different substituents from the group consisting of fluorine, chlorine, bromine, nitro, cyano, hydroxyl, straight-chain or branched alkyl, alkylthio and alkoxy having up to 6 carbon atoms, trifluoromethyl and trifluoromethoxy,
or a salt thereof.

2. A substituted N-(quinolin-2-yl-methoxy)benzylsulphonylurea or salt thereof according to claim 1, wherein
A, J, D, E, G, Z and M are identical or different and represent hydrogen, fluorine, chlorine, trifluoromethoxy or carboxyl,
represent straight-chain or branched alkyl having up to 8 carbon atoms, which is optionally substituted by hydroxyl, fluorine, chlorine or bromine,
represent straight-chain or branched alkoxy or alkoxycarbonyl having up to 8 carbon atoms, or
represent phenyl, which is optionally substituted by fluorine, chlorine, bromine, nitro, cyano or by straight-chain or branched alkyl or alkoxy having up to 6 carbon atoms,
$R^1$ represents straight-chain or branched alkyl having up to 8 carbon atoms, which is optionally substituted by hydroxyl, fluorine, chlorine, alkoxy having up to 6 carbon atoms or by cyclopropyl, cyclobutyl, cyclopentyl, cyclohexyl or cycloheptyl,
or represents cyclopropyl, cyclobutyl, cyclopentyl, cyclohexyl or cycloheptyl, which is optionally substituted by fluorine, chlorine, or straight-chain or branched alkyl having up to 6 carbon atoms,
$R^2$ and $R^3$ are identical or different and represent hydrogen or straight-chain or branched alkyl having up to 8 carbon atoms, which is optionally substituted by fluorine or chlorine, and
$R^4$ represents straight-chain or branched alkyl having up to 8 carbon atoms, which is optionally substituted by fluorine, chlorine, nitro, cyano, hydroxyl or by phenyl, or represents phenyl, which is optionally substituted by up to 2 identical or different substituents from the group consisting of fluorine, chlorine, bromine, nitro, cyano, hydroxyl, straight-chain or branched alkyl, alkylthio and alkoxy having up to 6 carbon atoms, trifluoromethyl and trifluoromethoxy.

3. A substituted N-(quinolin-2-yl-methoxy)benzylsulphonylurea or salt thereof according to claim 1, wherein A, J, D, E, G, Z and M are identical or different and represent hydrogen, fluorine, chlorine, or straight-chain or branched alkyl or alkoxy having up to 6 carbon atoms, R¹ represents straight-chain or branched alkyl having up to 6 carbon atoms, which is optionally substituted by fluorine, chlorine or alkoxy having up to 4 carbon atoms or by cyclopropyl, cyclopentyl or cyclohexyl, or represents cyclobutyl, cyclopentyl, cyclohexyl or cycloheptyl, which is optionally substituted by straight-chain or branched alkyl having up to 4 carbon atoms or by fluorine, R² and R³ are identical or different and represent hydrogen or straight-chain or branched alkyl having up to 6 carbon atoms, and R⁴ represents straight-chain or branched alkyl having up to 6 carbon atoms, which is optionally substituted by fluorine, chlorine or phenyl, or represents phenyl, which is optionally substituted by fluorine, chlorine, bromine or by straight-chain or branched alkyl having up to 4 carbon atoms.

4. A compound according to claim 1, wherein the quinolylmethoxy grouping on the phenyl ring is in the 4-position relative to the N-substituted sulphonylurea group.

5. A compound according to claim 1, wherein such compound is N-(4-toluenesulphonaminocarbonyl)-1-[4-(quinolin-2-yl-methoxy)phenyl]-1-pentylamine of the formula

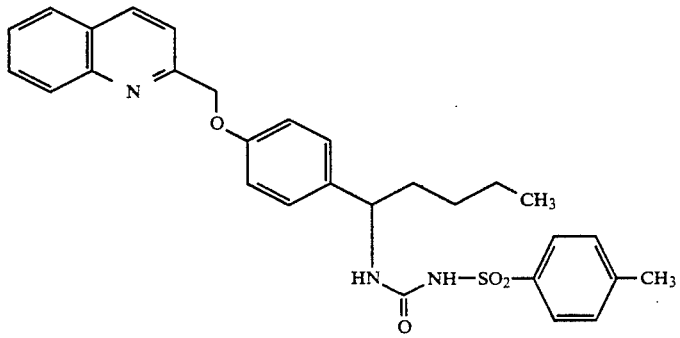

or a salt thereof.

6. A compound according to claim 1, wherein such compound is N-(2-toluenesulphonaminocarbonyl)-[4-(quinolin-2-yl-methoxy)phenyl]-cyclopentyl-methylamine of the formula

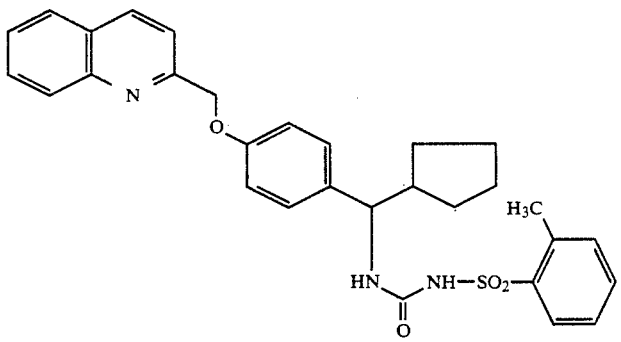

or a salt thereof.

7. A leucotriene synthesis-inhibiting composition comprising an amount effective therefor of a compound or salt according to claim 1 and a pharmaceutically acceptable diluent.

8. A method of inhibiting leucotriene synthesis in a patient in need thereof which comprises administering to such patient an amount effective therefor of a compound or salt according to claim 1.

9. The method according to claim 8, wherein such compound is
N-(4-toluenesulphonaminocarbonyl)-4-[4-(quinolin-2-yl-methoxy)phenyl]-1-pentylamine or
N-(2-toluenesulphonaminocarbonyl)-[4-(quinolin-2-yl-methoxy)phenyl]-cyclopentylmethylamine
or a salt thereof.

* * * * *

UNITED STATES PATENT AND TRADEMARK OFFICE
CERTIFICATE OF CORRECTION

PATENT NO. : 5,179,106

DATED : January 12, 1993

INVENTOR(S) : Mohrs et al.

It is certified that error appears in the above-identified patent and that said Letters Patent is hereby corrected as shown below:

Col. 14, line 27    Delete " or by aryl having 6 to 10 carbon atoms, "

Signed and Sealed this

Fifth Day of July, 1994

Attest:

BRUCE LEHMAN

*Attesting Officer*    *Commissioner of Patents and Trademarks*